United States Patent [19]

Di Mucci

[11] 4,155,366

[45] May 22, 1979

[54] METHOD OF PERCUTANEOUS PAIN ALLEVIATION

[75] Inventor: Jerry Di Mucci, Hauppauge, N.Y.

[73] Assignee: Ultra-Aids, Inc., Hicksville, N.Y.

[21] Appl. No.: 797,025

[22] Filed: May 16, 1977

Related U.S. Application Data

[63] Continuation-in-part of Ser. No. 584,959, Jun. 9, 1975, abandoned.

[51] Int. Cl.² ............................................. A61N 1/36
[52] U.S. Cl. ................................................. 128/421
[58] Field of Search .................... 128/419 R, 421, 422

[56] References Cited

U.S. PATENT DOCUMENTS

| | | | |
|---|---|---|---|
| 3,025,858 | 3/1962 | Browner | 128/422 |
| 3,209,081 | 9/1965 | Ducote et al. | 128/419 R |
| 3,518,996 | 7/1970 | Cortina | 128/422 |
| 3,768,486 | 10/1973 | Berkovits et al. | 128/422 |
| 3,893,462 | 7/1975 | Manning | 128/421 |

*Primary Examiner*—William E. Kamm
*Attorney, Agent, or Firm*—Hane, Roberts, Spiecens & Cohen

[57] ABSTRACT

A method for effecting percutaneous pain allevation in which sawtooth shaped electrical pulses are produced at electrodes for percutaneous application to bodily areas experiencing pain. The electrical pulses may be selectively varied in amplitude in the range of zero to about 100 volts peak-to-peak, the pulse repetition frequency may be selectively varied in the range of about 10 HZ to 100 HZ, and the output current is from 1 MA to 40 MA. In addition, the output electrode is located at the site of the pain and the return electrode is located on the body at distance in the range of 7 cm to 20 cm from the output electrode.

There is also disclosed a method for pain alleviation utilizing electric pulses having the above-described parameters.

3 Claims, 5 Drawing Figures

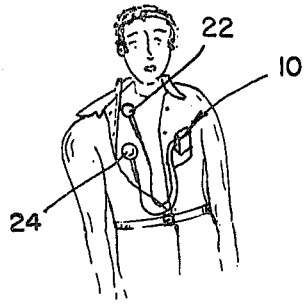
FIG. 1
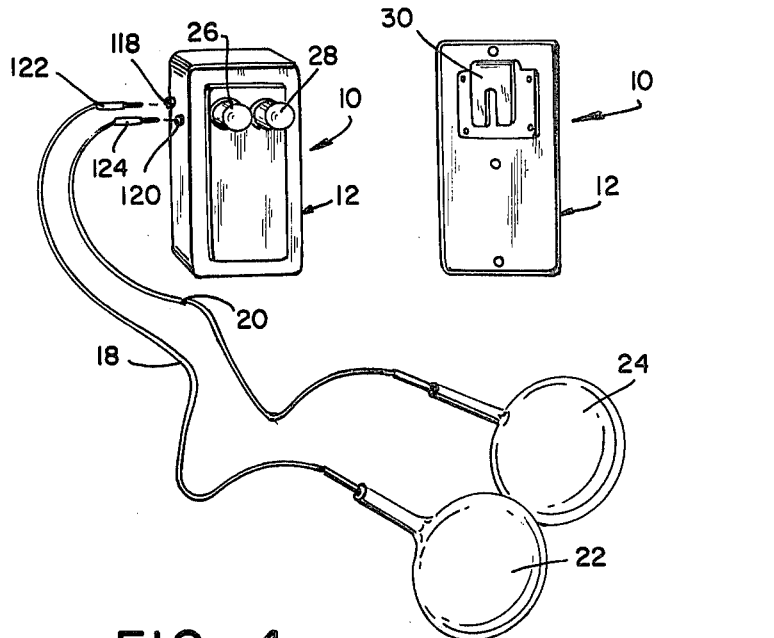
FIG. 2
FIG. 3
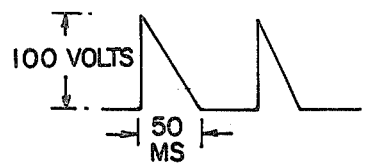
FIG. 5
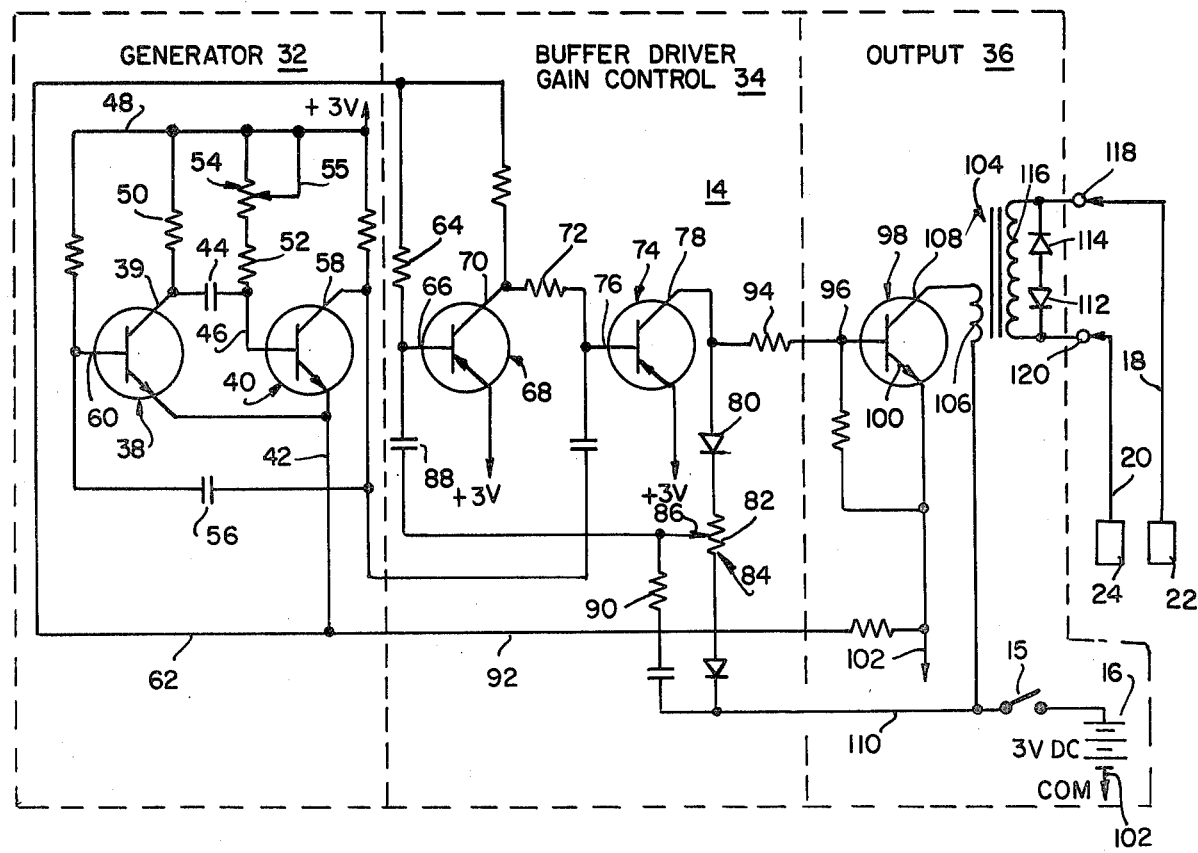
FIG. 4

4,155,366

METHOD OF PERCUTANEOUS PAIN ALLEVIATION

CROSS REFERENCE TO RELATED APPLICATIONS

This application is a Continuation-in-part of my co-pending application Ser. No. 584,959, filed June 9, 1975 and now abandoned.

BACKGROUND OF THE INVENTION

The present invention relates to methods for electrical treatment of body tissues and muscles and more particularly to percutaneous pain alleviation by application of electrical pulses to external areas of the human body experiencing pain.

Electrical pulse generators have long been known for use for various medical purposes. The use of such devices, however, has been limited due to the sometimes painful and noxious side effects porduced by such devices. Such undesirable side effects have been variously attributed to excessive voltages, improper pulse frequencies and/or wave shapes and unduly lengthy periods of application of the electrical pulses to the body. The cumbersome and unwieldy bulk and weight of such known devices has further limited the use of such devices at fixed locations, to wit, at the physician's office, the home, etc.

It is therefore an object of the present invention to provide a pain alleviation method and a method of percutaneous pain alleviation in which the amplitude and pulse repetition frequency of the electrical output pulses is selectively variable by the user.

It is a further object of the present invention to provide a percutaneous pain alleviator for carrying out the method described which is compact, lightweight and suitable for concealed wear by the user.

SUMMARY OF THE INVENTION

In accordance with the principles of the present invention there is provided a method for effecting percutaneous pain alleviation comprising producing electrical output pulses of a preselected wave-shape, selectively varying the amplitude of the output pulses and the pulse repetition frequency of the output pulses and applying the output pulses percutaneously.

According to another aspect of the invention, there is contemplated a method of alleviating pain at a portion of a body by applying via external electrodes electrical pulse signals having right-angled sawtooth waveforms with a pulse repetition frequency in the range of about 10 to about 100 Hz, a voltage amplitude in the range of about 1 to about 100 volts and a current in the range of 1 MA to about 40 MA.

BRIEF DESCRIPTION OF THE DRAWINGS

Further objects, features and advantages of this invention will become apparent from a consideration of the following description, the appended claims and the accompanying drawing, in which:

FIG. 1 is a pictorial illustration showing the manner of use of the device of the present invention;

FIG. 2 is a front perspective view of the device for carrying out the method of the present invention;

FIG. 3 is a rear view of the device of FIG. 2;

FIG. 4 is an electrical schematic diagram of the device of FIG. 2; and

FIG. 5 is a waveform diagram of the output pulses of the device of FIG. 2.

DETAILED DESCRIPTION OF THE INVENTION

In the drawing and in particular FIGS. 1–3 thereof a percutaneous pain alleviator device for carrying out the method of the present invention is generally designated by the numeral 10.

Device 10 comprises a pocket size housing 12 enclosing an electrical pulse generator 14 including a battery 16 (shown in FIG. 4) and a pair of detachable output electrodes 18, 20 respectively terminating in disc-shaped applicator probes 22, 24 of a conductive elastomer. Device 10 is provided with a pair of rotatable control knobs 26, 28 for respectively controlling the magnitude of the output voltage and pulse repetition frequency of the output pulses obtained at output electrodes 18 and 20.

In addition, housing 12 may be provided with a mouting clip 30 on the back face thereof for convenience in wearing device 10 when attached to a shirt pocket as shown in FIG. 1 or any other suitable article of clothing.

Referring to FIG. 4, pulse generator circuit 14 comprises a generator stage 32, a buffer driver and gain control stage 34 and an output stage 36.

Generator stage 32 is an emitter-coupled free-running multivibrator comprising a pair of transistors 38 and 40 having their emitters jointly connected by lead 42, with the collector 39 of transistor 38 being connected through coupling capacitor 44 to the base 46 of transistor 40. Collector 39 is connected to bias supply line 48 through resistor 50 while base 46 is connected to supply line 48 through fixed resistor 52 and variable pulse repetition frequency control resistor 54 in series therewith. Coupling capacitor 56 feeds the pulse output at collector 58 of transistor 40 back to the input base 60 of transistor 38.

The pulse output of generator stage 32 appearing on emitter lead 42 is applied through lead 62 and resistor 64 to the input of buffer driver stage 34 at base 66 of transistor 68. The output of buffer transistor 68 taken at collector 70 is applied via resistor 72 to the input of transistor 74 at its base 76. Collector 78 is connected through diode 80 to one end of the resistor arm 82 of gain control potentiometer 84, of which wiper arm 86 is connected to base 66 through coupling capacitor 88 and through resistor 90 to lead 92. The other end of resistor arm 82 is connected to lead 92.

The pulse output from transistor 74 taken at collector 78 is applied via resistor 94 to the base of output transistor 98, while emitter 100 is connected to common terminal 102.

Transformer 104 has its primary winding 106 connected across collector 108 of transistor 98 and bias supply lead 110. The back-to-back arrangement of diodes 112 and 114 is connected across transformer secondary winding 116, with the output terminal jacks 118 and 120 being taken across secondary winding 116.

Output electrodes 18 and 20 may be releasably connected to output jacks 118 and 120 by means of electrode plugs 122 and 124 affixed to the respective ends of electrodes 18 and 20.

Output jack 118, plug 122 and applicator probe 22 may be colored red signifying the "positive" electrode and jack 120, plug 124 and probe 24 colored black signifying the "negative" electrode.

The pulse output at output terminals 118 (FIG. 5) is a right angle sawtooth waveform with a perpendicular leading edge and a sloped trailing edge and having a selectively variable amplitude ranging from zero to 100 volts peak-to-peak, a selectively variable pulse repetition frequency ranging from 10 HZ to 100 HZ, and a current ranging from 1 to 40 MA. The amplitude may be selectively varied by potentiometer arm 86 which is mechanically connected to voltage amplitude control knob 26, while the pulse repetition frequency (p.r.f.) may be selectively varied by variable resistor 54 whose wiper arm 55 is connected to frequency control knob 55.

A power on-off switch 15 is connected between the positive terminal of battery 16 and lead 110 for selective connection of battery 16 when device 10 is in use and disconnection when not in use.

In operation, with both electrodes 18 and 20 connected, the wearer applies positive electrode probe 22 directly on the bodily area experiencing pain and the negative electrode pad 24 on the body at a position of 7 to 20 cm (preferably from 10 to 15 cm) away from positive electrode pad 22. In order to ensure adherence of pads 22 and 24 to the bodily skin area, a non-allergic neutral water soluble jelly, such as type K-Y jelly marketed by Johnson & Johnson may be applied to the relevant bodily areas.

The wearer may then adjust the magnitude and frequency of the pulse output being applied by manipulating knobs 26 and 28 respectively until he arrives at an optimum voltage magnitude and p.r.f., which provides the greatest degree of pain relief and freedom from noxious side effects, i.e., greatest comfort. It has been found that pain relief is usually obtained within about fifteen minutes of application of device 10 and that for best results in many instances the application should continue for about fifteen minutes after substantial pain relief is experienced.

Several clinical tests were caused to be made by a medical physician to prove the utility of the present invention and several specific examples are set forth below.

TEST No. 1

The subject of this test was male, Caucasian, and 65 years of age, who three years prior to this test suffered a slipped disc between lumbar vertebrae 4 and 5, resulting in temporary paralysis for a period of about two months. Since patient declined corrective surgery, he was treated by bilateral leg traction, bed rest and physical therapy and after four monts of such treatment, subject returned to part time work as a physician. However, after two months of such activity, he suffered a relapse and was placed on nonoperative conservative treatment. Subject is presently retired but is mobile with the aid of a back brace.

Physical examination of the subject revealed bilateral muscle atrophy of both legs. Laboratory workups are within normal limits. An electrocardiagram (E.K.G.) showed a bifascicular block.

The subject's major complaint was the occurrence of frequent attacks of sharp radiating pain along the course of the left sciatic nerve, these attacks resulting in instant collapse of muscular power of both lower extremeties.

The subject was subjected to treatments daily over the past three months by alleviator device 10 in which the applied output voltage was 100 volts peak-to-peak at a p.r.f. of 100 HZ for about fifteen to thirty minutes. As a result, patient reports minimal to moderate pain in the affected areas and very infrequent attacks of such pain. Only a minimal amount of narcotics is being administered to help alleviate the reduced pain.

TEST No. 2

The subject of this test was male, Caucasian and 61 years of age and had far advanced bilateral osteoarthritic changes of both hips and, in addition, sustained a moderate-to-massive posterior wall infarct in 1950. His E.K.G. indicated a complete A.V. block and venticular arrhythmia. In early 1960 an Austin Moore prothesis was placed in his left hip. Two days following surgery, the subject suffered a mild pulmonary embolism, but recovered. However, shortly after surgery, the Austin Moore prothesis proved to be unstable resulting in an actual shortening by 1½ inches of his left lower extremities.

The subject's cardiac status precluded any further surgical procedure and the pain in his lower extremities became excrutiating and various forms of narcotics were administered to no avail.

The subject was then subjected to treatment by alleviator device 10 in which the voltage was set to 100 volts peak-to-peak and the p.r.f. at 100 HZ, by applying the device to the right hip resulting in dramatic alleviation of pain. Another alleviator device 10 was applied to the subject's left hip with similar pain alleviation results. These treatments were applied for periods of about thirty minutes daily over a period of about six months, with the subject reporting an approximate 60% pain relief without the aid of any form of narcotics.

TEST No. 3

The subject of this test was male, Caucasian, and 67 years of age and was seen by a physician about five months prior to this test when he complainded of osteoarthritic changes in both hips and numbness of both feet. A thorough workup by an orthopedic surgeon, and internist and a cardiovascular surgeon revealed no major pathological finding to account for his symptoms except X-ray findings of bilateral osteoarthritic changes of the hips and the lumbar vertebrae.

Alleviator device 10 was applied to the subject, with positive electrode 18 being applied to the mid lumbar area and negative electrode 20 applied alternately to the right and left thighs. The voltage applied was 60 volts peak-to-peak at a p.r.f. of 60 HZ. Upon two such treatments for about thirty minutes the subject experienced relief of numbness in his feet. The subject continues to use alleviator device 10 thus experiencing virtually complete pain relief.

TEST No. 4

The subject of this test was male, Caucasian, 57 years of age and had an abdominal-perineal resection six years prior to this test. His main complaints were that he suffered severe pain in the sacral area and along the right sciatic nerve distribution along the Gluteal folds, requiring him to remain in bed. A workup of the subject showed a normal laboratory blood test and no bony metastasis, the pain being a sequel to surgery.

Alleviator device 10, at 20 volts peak-to-peak and at a p.r.f. of 20 HZ, was applied to the patient for a period of about thirty minutes. As a result, complete pain relief was achieved and the subject was thereafter able to walk.

In other tests, some subjects required treatments by alleviator device 10 for periods of only a few minutes before experiencing pain alleviation, whereas in other tests the subjects found it necessary to maintain the treatment continuously for many hours or even days in order to achieve a satisfactory degree of pain alleviation.

Tests have shown that the p.r.f. to be effective without side effects or burns must be in the range of 10 to 100 HZ. In fact, when frequencies in the range of 500 to 5000 HZ have been used skin irritation has been found. In addition, the 10 to 100 HZ range permits the use of multiple sets of electrodes in parallel with the original set of electrodes.

Although the invention has been described with reference to a particular embodiment thereof, it is to be understood that this embodiment is merely illustrative of the application of the principles of the invention. Numerous modifications may be made therein and other arrangements may be devised without departing from the spirit and scope of the invention.

What is claimed is:

1. The method of alleviating pain at a portion of the body comprising the steps of generating electrical pulse signals having a right-angled sawtooth waveform with a pulse repetition frequency in the range of about 10 HZ to about 100 HZ, a voltage amplitude in the range of about 1 volt to about 100 volts, and a current amplitude in the range of 1 MA to about 40 MA, feeding the electrical pulses across a pair of electrodes, applying one electrode to the skin at the portion of the body experiencing pain, and applying the other electrode to skin at a distance of from seven to twenty centimeters from said one electrode whereby the electrical pulse signals block the pain at said portion of the body.

2. The method of claim 1 wherein said distance is from ten to fifteen centimeters.

3. The method of claim 1 wherein the sawtooth waveform has perpendicular leading edges and sloping trailing edges.

* * * * *